(12) United States Patent
Chesnin

(10) Patent No.: US 8,137,326 B2
(45) Date of Patent: Mar. 20, 2012

(54) HUB FOR TRIPLE LUMEN CATHETER ASSEMBLY

(75) Inventor: Kenneth Chesnin, Philadelphia, PA (US)

(73) Assignee: Medical Components, Inc., Harleysville, PA (US)

( * ) Notice: Subject to any disclaimer, the term of this patent is extended or adjusted under 35 U.S.C. 154(b) by 906 days.

(21) Appl. No.: 11/800,353

(22) Filed: May 4, 2007

(65) Prior Publication Data

US 2007/0260221 A1    Nov. 8, 2007

Related U.S. Application Data

(60) Provisional application No. 60/798,215, filed on May 5, 2006.

(51) Int. Cl.
*A61M 25/00* (2006.01)

(52) U.S. Cl. .......... 604/284; 604/21; 604/93.01

(58) Field of Classification Search .......... 604/21, 604/93.01, 523, 264, 272, 533, 284, 285, 604/43, 506, 164.01, 164.04
See application file for complete search history.

(56) References Cited

U.S. PATENT DOCUMENTS

| | | | |
|---|---|---|---|
| 4,037,599 A * | 7/1977 | Raulerson | 604/44 |
| RE31,873 E | 4/1985 | Howes | |
| 4,670,009 A | 6/1987 | Bullock | |
| D303,712 S | 9/1989 | Goldberg | |
| 5,059,170 A * | 10/1991 | Cameron | 604/43 |
| 5,135,599 A | 8/1992 | Martin et al. | |
| 5,167,623 A | 12/1992 | Cianci et al. | |
| 5,178,678 A | 1/1993 | Koehler et al. | |
| 5,195,962 A | 3/1993 | Martin et al. | |
| 5,221,256 A | 6/1993 | Mahurkar | |
| 5,378,230 A | 1/1995 | Mahurkar | |
| 5,472,417 A | 12/1995 | Martin et al. | |
| 5,486,159 A | 1/1996 | Mahurkar | |
| 5,556,390 A | 9/1996 | Hicks | |
| 5,718,678 A * | 2/1998 | Fleming, III | 604/43 |
| 5,749,889 A | 5/1998 | Bacich et al. | |
| 5,781,678 A * | 7/1998 | Sano et al. | 385/45 |
| 5,810,776 A * | 9/1998 | Bacich et al. | 604/131 |
| 5,947,953 A | 9/1999 | Ash et al. | |
| 6,086,564 A * | 7/2000 | McLaughlin | 604/179 |
| 6,146,354 A | 11/2000 | Beil | |
| 6,592,544 B1 * | 7/2003 | Mooney et al. | 604/43 |

(Continued)

OTHER PUBLICATIONS

International Search Report dated Sep. 10, 2008, PCT/US07/10971 (2 pages).

(Continued)

*Primary Examiner* — Quynh-Nhu H Vu
(74) *Attorney, Agent, or Firm* — Glenn M. Massina; Fox Rothschild LLP

(57) ABSTRACT

A hub (14) for a triple lumen catheter (12) especially for use with a catheter assembly (10) such as for hemodialysis. The hub (14) has a body (40) with one distal opening (58) for insertion thereinto of a proximal end portion (26) of the catheter (12), and three proximal openings (52,54,56) for insertion thereinto of distal end portions (74,76,78) of three extension tubes (16,18,20) each associated with one of the catheter's three lumens (30,32,34). The hub provides three passageways (68,70,72) extending from respective proximal openings to respective interior openings (60,62,64) in communication with the one distal opening (58), for establishing fluid communication between each extension tube (16,18,20) and its associated catheter lumen (30,32,34). Preferably, the hub is insert molded to respective end portions of the catheter (12) and the extension tubes (16,18,20).

25 Claims, 3 Drawing Sheets

U.S. PATENT DOCUMENTS

| | | | |
|---|---|---|---|
| 6,689,096 B1* | 2/2004 | Loubens et al. | 604/96.01 |
| 6,695,832 B2* | 2/2004 | Schon et al. | 604/544 |
| 6,827,710 B1* | 12/2004 | Mooney et al. | 604/500 |
| 7,311,697 B2* | 12/2007 | Osborne | 604/524 |
| 7,347,853 B2* | 3/2008 | DiFiore et al. | 604/537 |
| 7,901,395 B2* | 3/2011 | Borden et al. | 604/523 |
| 2003/0055387 A1* | 3/2003 | Sutton et al. | 604/284 |
| 2004/0068248 A1* | 4/2004 | Mooney et al. | 604/500 |
| 2006/0089604 A1 | 4/2006 | Guerrero | |
| 2008/0082079 A1 | 4/2008 | Braga et al. | |

OTHER PUBLICATIONS

Written Opinion dated Sep. 10, 2008, PCT/US07/10971 (3 pages).
International Preliminary Report; Jun. 9, 2009; PCT/US07/10971.
European Search Report dated May 8, 2009; EP 07794591.3 (5 pages).

* cited by examiner

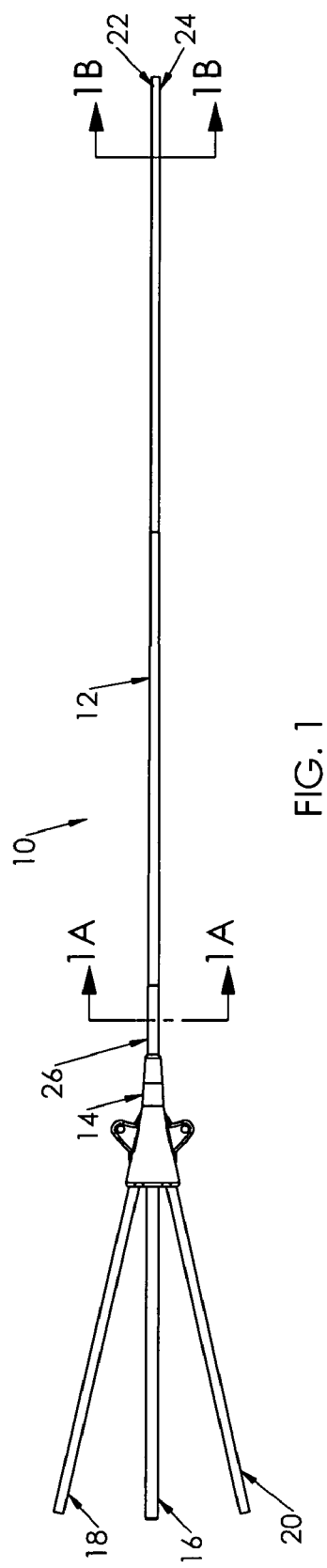
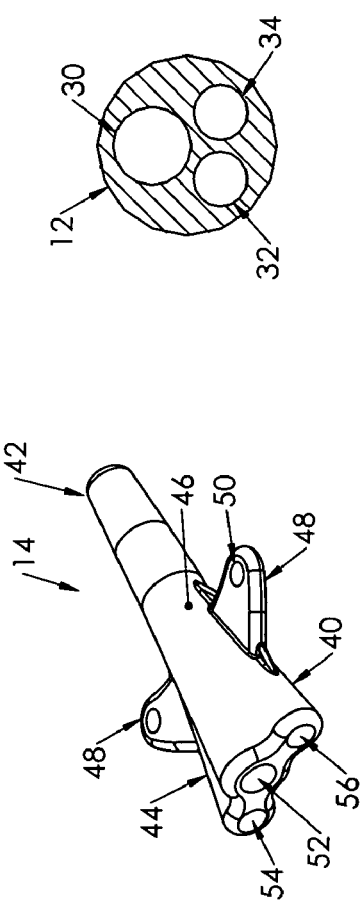
FIG. 1
FIG. 1A
FIG. 1B
FIG. 2

HUB FOR TRIPLE LUMEN CATHETER ASSEMBLY

CROSS-REFERENCE TO RELATED APPLICATIONS

This application claims the benefit of U.S. Provisional Patent Application Ser. No. 60/798,215 filed May 5, 2006.

FIELD OF THE INVENTION

This relates to the field of medical devices and more particularly to catheters and catheter assemblies.

BACKGROUND OF THE INVENTION

A catheter assembly may have more than one lumen, and usually such a multilumen catheter has an extension tube connected to the proximal end of each of the lumens on that portion of the proximal end of the assembly that is disposed outside the patient. Usually, the catheter assembly is secured to the torso of the patient in a manner to prevent any dislocation of the distal tips of the catheter lumens from any movement along the vessel after initial placement at the catheterization site. However, certain catheter assemblies, termed PICC catheters (for peripherally inserted central catheters), are implanted through a vessel entry on an arm of the patient, known as axillary placement. The remainder of the catheter is disposed in the vasculature of the patient (the distal end portion) or in a subcutaneous tunnel in order to anchor the catheter assembly against any movement that would dislodge the position of the distal tip of the catheter from its precisely selected location in the patient's vasculature. Such implanted catheters are used for various procedures such as hemodialysis, infusion therapy and power injection such as of contrast agent.

The distal ends of the extension tubes enter the proximal end of a hub in order to be put in sealed fluid communication with proximal ends of respective lumens of the catheter that enter the distal end of the hub. Luer connectors are affixed on the proximal ends of the extension tubes for connection to and disconnection from tubing of the dialysis machine or other medical device, and a clamp such as a Roberts clamp is disposed along the length of each extension tube in order to be manipulated into a clamping state that prevents fluid flow through the extension tube while permitting fluid flow therethrough when manipulated into an unclamping state. The material of the extension tubes is selected such that it is better able to resume its full diameter when the clamp is unclamped.

It is desired to provide a low profile hub for establishing the connections of three extension tubes to the proximal ends of respective lumens of a triple lumen catheter, especially for PICC catheter assemblies, where the hub is located along the patient's arm.

BRIEF SUMMARY OF THE INVENTION

The present invention is a hub to connect the distal ends of three extension tubes to proximal ends of respective lumens of a triple lumen catheter for fluid communication therewith. The hub has a low profile, and the extension tubes extend from the hub proximal end at small angles from one another both horizontally and vertically; the distal end portion of the central extension tube of the three is relatively slightly elevated within its respective hub passageway to allow such small angles and the close spacing of the three distal end portions of the three lumens, whereby the proximal hub end is narrowed in width while only being minimally increased in height when compared to a hub wherein the three extension tubes are coplanar.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a plan view of a triple lumen catheter assembly and having a catheter, a hub and three extension tubes;

FIGS. 1A and 1B are cross-sectional views of the catheter near the proximal end of the catheter and near the distal end thereof, respectively;

FIG. 2 is an isometric view of the proximal end of the hub of FIG. 1 without the catheter and extension tubes;

DETAILED DESCRIPTION OF THE INVENTION

Figure 4:
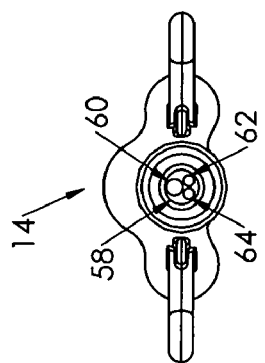
FIGS. 3, 4 and 5 are, respectively, a top view, a distal view and a proximal view of the hub of FIG. 2.

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Figure 6:
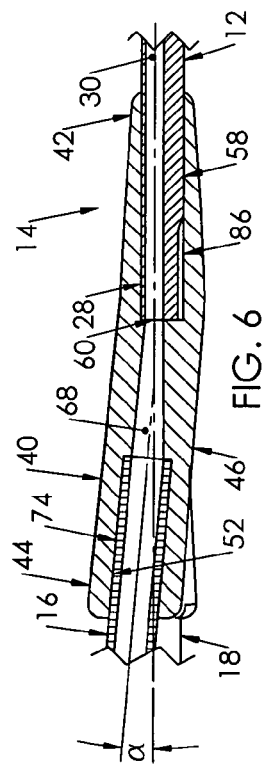
FIGS. 6 and 7 are, respectively, a longitudinal side cross-section taken along lines 6-6 of FIG. 5 (the vertical medial plane), and a longitudinal top cross-section taken along lines 7-7 thereof (the horizontal medial plane), and end portions of the catheter and extension tubes are seen disposed along respective openings within the hub.

A catheter assembly 10 is seen in FIG. 1 to include a triple lumen catheter 12, a hub 14 and three extension tubes 16, 18, 20. Catheter 12 includes a distal end portion 22 extending to a distal tip 24, and also a proximal end portion 26 that extends to a proximal end 28 (FIG. 6). As illustrated in FIGS. 1A and 1B, catheter 12 has a large diameter lumen 30 and two relatively smaller diameter lumens 32, 34, all of which slightly decrease in diameter from proximal end portion 26 to distal end portion 22, although, optionally, their diameters may be held constant. The three lumens are shown as each having a circular cross-section, although, optionally, their cross-sections may have some other shape such as oval, generally triangular, or semi-cylindrical. The outside diameter of the catheter is seen to have a larger diameter at the proximal end portion and a somewhat smaller diameter at the distal end portion, although the diameter may remain constant if desired. Preferably, although not shown, at the distal end portion of catheter 12, the two smaller diameter lumens 32, 34 may have their distal tip openings at one selected location (or respective selected locations) while the larger diameter lumen 30 continues distally therefrom to a distal tip opening that is spaced axially distally from the distal tip openings of the two smaller lumens 32, 34. The larger lumen 30 would serve to provide the lumen for insertion therethrough of the guide wire utilized during placement of the catheter in the vasculature of the patient.

Figure 3:
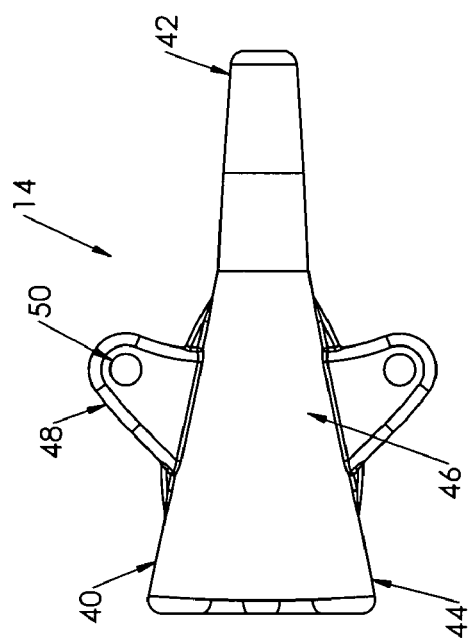

Hub 14 in FIGS. 2 to 4 is seen to have a hub body 40 with a distal end 42, a proximal end 44 and a central section 46 laterally outwardly from which extend a pair of suture wings 48 with suture openings 50 therethrough to facilitate anchoring the hub to the patient after the catheter implantation procedure has been completed. Hub 14 is preferably insert molded about the proximal end portion of the catheter and the distal end portions of the extension tubes, but will be described as if it were a premolded body. Openings 52, 54, 56 for the three extension tubes are seen at the proximal end 44 of hub 14, while the proximal end 28 will be inserted into a distal opening 58 (FIGS. 6 and 7) at distal end 42. (If the hub is being premolded, then each opening would conclude at a respective ledge against which the distal end of a respective extension tube would abut upon full insertion thereinto.)

Figure 5:
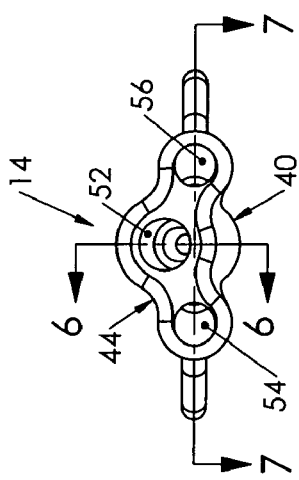

Also seen in FIGS. 4 and 5, the surfaces in contact with the eventual patient are rounded thus minimizing tissue stress, and the bottom surface of hub body 40 is contoured to provide shallow "breathing" channels extending distally from the proximal end, that permit the skin of the eventual patient to breathe and thereby help avoid tissue damage. The overall size of hub body 40 is of a low profile design and is of decreased intrusiveness, less likely to be snagged, thereby resulting in better healing at the exit site of the catheter from the patient's body.

It is seen in FIG. 4 that distal opening 58 includes three discrete interior openings 60, 62, 64 at its proximal end 66 that communicate with respective passageways 68, 70, 72 inwardly from the distal end 42 of hub body 40. It is seen that interior opening 60 is larger in diameter than interior openings 62, 64 and in a relatively slightly raised position; the interior openings 60, 62, 64 are associated with lumens 30, 32, 34 of the catheter 12, shown in FIG. 1A. Proximal opening 52 is larger in diameter than either of proximal openings 54, 56 and is located centrally and elevated relative thereto.

Figure 7:
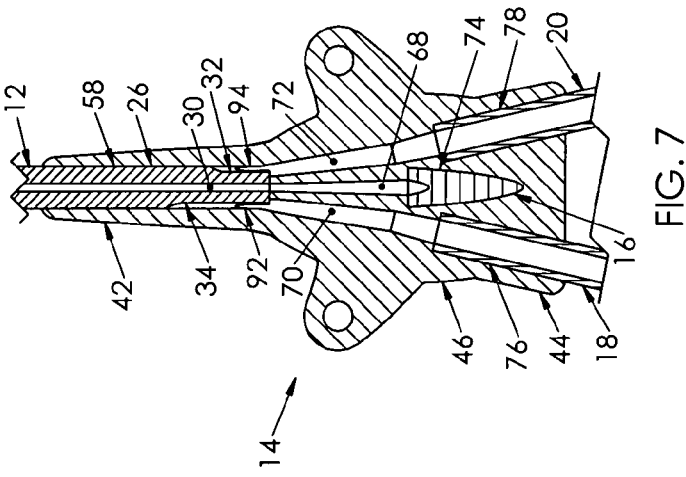

In FIGS. 6 and 7, hub 14 has a central passageway 68 that extends distally from proximal opening 52 to interior opening 60, and central passageway 68 is angled slightly upwardly relative to the medial plane of the hub body 40, thus slightly increasing the height of the hub body's proximal end than if all passageways (and their respective extension tubes) were coplanar. The hub body 40 has two passageways 70, 72 of smaller diameter extending from respective interior openings 62, 64 to respective ones of proximal openings 54, 56 and that are angled slightly to diverge as they continue proximally from their respective interior openings but remain in the medial plane of the hub body, enabling the width of the hub proximal end to be narrower than if all three passageways (and their respective extension tubes) were coplanar. For small diameter catheter lumens, preferably the diameters of the extension tubes are of larger diameters to result in tubes that are sturdier, and the inner diameters are larger than those of the associated catheter lumens: therefore, each hub passageway tapers to a smaller diameter than that of the respective extension tube as the hub passageway extends distally from its junction with a respective proximal opening to its distal end junction with a respective interior opening. The passageways are also angled toward a relatively more co-parallel orientation as it joins its respective interior opening.

Figure 8:
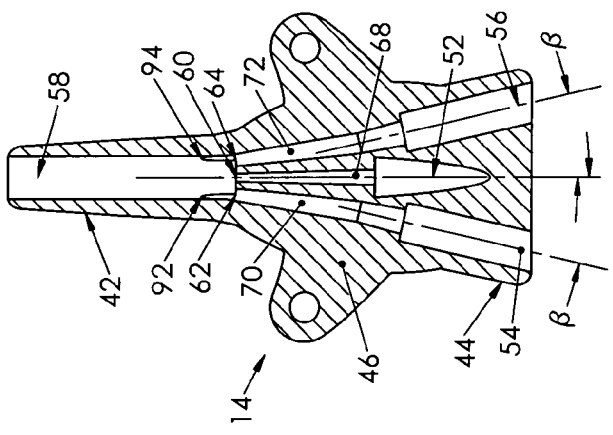
FIG. 8 is a cross-sectional view of the hub, similar to FIG. 7 but with the catheter and extension tubes removed to more clearly show the passageways of the hub.

Still referring to FIGS. 6 and 7, a proximal end portion of catheter 12 is shown disposed in distal opening 58. Distal end portions 74, 76, 78 of extension tubes 16, 18, 20 are shown disposed in respective proximal openings 52, 54, 56 and extending along portions of the respective passageways 68, 70, 72. FIG. 8 is a cross-sectional view of hub body 40 similar to FIG. 7 (taken along the horizontal medial plane of the hub) but with the catheter and extension tube portions removed to better display the passageways of the hub body and their junctions with respective proximal openings and interior openings. It may be seen that no portion of the three passageways is disposed in a vertical overlap with another passageway; with this design aspect, insert molding may be done inexpensively with a two-draw mold with a generally horizontal parting line but that is slightly raised centrally in the proximal end. Formation of the molded passageways utilizes core pins, as is conventional; where the hub body is insert molded over the extension tube end portions, the core pins may extend as mandrels at least through the extension tubes.

Figure 9:
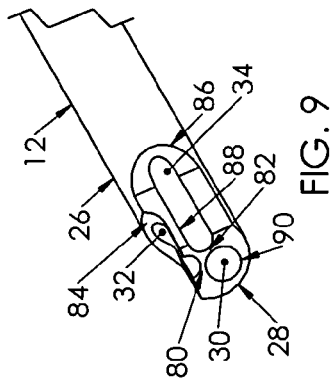
FIG. 9 is a partial cross-section of the proximal end of the catheter (inverted) that is skived at the two smaller lumen ends to facilitate fluid connection with the respective two passageways and thus the respective extension tubes in the hub of the present invention, during insert molding of the hub body to the respective end portions of the catheter and extension tubes.

Referring now to FIG. 9 and FIGS. 6 and 8, the proximal end of the catheter 12 (shown inverted in FIG. 9) is skived to provide assured fluid communication with the passageways of the hub 14, at least where the hub is insert molded therearound. Material is removed from outer walls of each smaller lumen 32, 34 and larger lumen 30, such as by hot knife or razor blade, leaving wall sections 80, 82 remaining between each smaller lumen and larger lumen 30, mostly leaving intact the wall 90 defining the larger lumen 30 and the wall section 88 between the two smaller lumens. FIG. 9 shows that skiving may vary in length between the two sides of the catheter, with a longer length of one 86 thereof relative to the length of the other 84 allowing for increased molding material separating each of the lumens of the catheter added during the insert molding procedure, and also providing increased surface area for joining of the molding material to the catheter material, which in turn better prevents cross-lumen leakage and allows for greater working pressures inside the hub, for example, during power injection. For example, one skived length 84 may be 0.150 in (3.8 mm) while the other 86 may be 0.250 in (6.4 mm).

Within distal opening 58 of hub body 40, ledges 92, 94 may be provided extending from respective interior openings 62, 64 for the full lengths of the respective skived catheter wall sections 84, 86, in order to join with the wall sections to completely isolate the openings of the two lumens to assure separate fluid communication with respective passageways of the hub body. In an embodiment where the hub body is premolded, the walls of the catheter proximal end would be fused or bonded to the adjacent portions of the hub body 40. Techniques for such fusing or bonding may be by ultrasonic welding, radio frequency heating, adhesive, or a combination thereof, preferably facilitated by using precisely shaped and sized mandrels (not shown).

The hub of the present invention could be effectively utilized with a catheter 12 of a general outer diameter of up to 11 French, and may also be effectively utilized with a catheter of a general outer diameter of less than 5 French at its distal end, or about 0.066 in (1.7 mm). In such a small catheter, the larger lumen 30 could have an inner diameter (at least at its proximal end) of about 0.040 in (1.0 mm), while each of the two smaller lumens 32, 34 could have inner diameters each of about 0.028 in (0.7 mm). The extension tube 16 could have an outer diameter of about 0.106 in (2.7 mm), while extension tubes 18, 20 could each have an outer diameter of about 0.085 in (2.2 mm).

The overall width of the hub body at its distal end 42 could be about 0.135 in (3.4 mm) while its proximal end 44 width could be about 0.473 in (12 mm), and at suture wings 48 about 0.710 in (18 mm). The hub's length could be about 1.15 in (29 mm). The distal opening 58 of the hub and the proximal openings 52, 54, 56 could have inner diameters that are incrementally larger than the outer diameters of the extension tubes and catheter proximal end, respectively. The diameters of the passageways 68, 70, 72 could taper from proximal end diameters of about 0.066 in and 0.045 in (1.7 mm and 1.1 mm), respectively, to distal end diameters of about 0.040 in and 0.028 in (1.0 mm and 0.7 mm) at respective interior openings 60, 62, 64. The angle of elevation α of the larger passageway 68 within the vertical medial plane could be about 5° from horizontal (see FIG. 6); the angles β of each smaller passageway 70, 72 within the horizontal medial plane could be about 13° laterally from the vertical medial plane (see FIG. 8). The material from which hub 14 is manufactured could be polyurethane, for example.

It may be discerned that the design of the hub body of the present invention is such that only the distal end portion need be changed, as a function of the catheter lumen diameter, the distal opening diameter and the passageway diameters changing to accommodate catheters of greatly varying size, almost all by use of core pins without modifying the overall length, width and height of the hub body and minimizing production costs. The offset shape of the hub body allows for greater separation between the extension tubes, and permits varying the diameter of the proximal openings and the respective passageways to accommodate different sizes of extension tubes and/or catheter lumens. Further, the larger size proximal opening and passageway and interior opening is more or less straight, permitting relatively straight access with the larger lumen of the catheter for easier insertion and removal of guidewires, stylets, or other similar devices through the hub.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A hub for a triple lumen implantable catheter for joining extension tubes to respective lumens thereof for fluid transmission therethrough, comprising:
   a catheter defines three lumens;
   a hub body having a distal end, a central section and a proximal end, the hub including a distal opening defining a distal axis and configured to contain therewithin a proximal end of the catheter, and three proximal openings each configured to contain therewithin distal ends of respective extension tubes, wherein the proximal end of the catheter is skived and defines first and second selected lengths of two of the lumens, wherein the first and second selected lengths differ in length from each other,
   the hub including three interior openings at a proximal end of the distal opening associated with respective ones of the three catheter lumens, and three passageways communicating between respective ones of the three interior openings and respective ones of the three proximal openings,
   wherein two outermost passageways are disposed at respective small angles from a vertical medial plane of the hub body at their proximal ends, and
   wherein the centermost passageway is angled upwardly at its proximal end at a small angle from horizontal.

2. The hub of claim 1, wherein the hub body includes a pair of suture wings on opposite sides of the central section.

3. The hub of claim 1, wherein the hub body is insert molded to a proximal end portion of the catheter and distal end portions of the respective extension tubes.

4. The hub of claim 1, wherein outer surfaces and corners are rounded to minimize patient discomfort.

5. The hub of claim 1, wherein a bottom surface includes shallow channels extending distally from the proximal hub body end.

6. The hub of claim 1, wherein in a premolded hub body, inner diameters of the proximal openings are incrementally larger than outer diameters of the three extension tubes, and an inner diameter of the distal opening is incrementally larger than an outer diameter of the catheter proximal end.

7. The hub of claim 1, wherein diameters of the three interior openings are approximately equal to inner diameters of the associated respective three catheter lumens, and diameters of the proximal ends of the passageways are approximately equal to inner diameters of the associated respective three extension tubes.

8. The hub of claim 7, wherein the passageway diameters gradually decrease from their proximal ends to their respective interior openings.

9. The hub of claim 7, wherein the three passageways are almost parallel at their distal ends and are more angled from each other at their proximal ends.

10. The hub of claim 1, wherein the two outermost passageways are disposed at respective angles of about 13° from a vertical medial plane of the hub body at their proximal ends.

11. The hub of claim 1, wherein the centermost passageway is angled upwardly at an angle of about 5° from horizontal.

12. An assembly of a triple lumen catheter, three extension tubes and a hub, comprising:
   a catheter adapted for implantation into vasculature of a patient and including at least a proximal end portion and three lumens extending therethrough for fluid transmission;
   three extension tubes each associated with a selected one of the three lumens of the catheter; and
   a hub body integrally joined to the proximal end portion of the catheter and to distal end portions of the three extension tubes and providing passageways extending and establishing sealed fluid communication between each extension tube and a respective selected one of the three lumens of the catheter,
   wherein the hub body contains the proximal end portion of the catheter within a distal opening and provides interior openings in communication with respective ones of the three lumens of the catheter, wherein the proximal end portion of the catheter is skived and defines first and second selected lengths of two of the lumens, wherein the first and second selected lengths differ in length from each other,
   the hub passageways extend from respective ones of the interior openings to respective proximal openings within which distal end portions of the respective extension tubes are contained, a centermost of the passageways extends proximally and upwardly at a small angle from horizontal and outermost ones of the passageways extend proximally and laterally outwardly at respective small angles from a vertical medial plane through the hub body.

13. The assembly of claim 12, wherein the hub body is insert molded about the proximal end portion of the catheter and the distal end portions of the extension tubes.

14. The assembly of claim 12, wherein the hub body includes a pair of suture wings on opposite sides of the central section.

15. The assembly of claim 12, wherein outer surfaces and corners are rounded to minimize patient discomfort.

16. The assembly of claim 12, wherein the bottom surface includes shallow channels extending distally from the proximal hub body end.

17. The assembly of claim 12, wherein in a premolded hub body, inner diameters of the proximal openings are incrementally larger than outer diameters of the three extension tubes, and an inner diameter of the distal opening is incrementally larger than an outer diameter of the catheter proximal end.

18. The assembly of claim 12, wherein diameters of the three interior openings are approximately equal to inner diameters of the associated respective three catheter lumens, and diameters of the proximal ends of the passageways are approximately equal to inner diameters of the associated respective three extension tubes.

19. The assembly of claim 18, wherein the passageway diameters gradually decrease from their proximal ends to their respective interior openings.

20. The assembly of claim 18, wherein the three passageways are almost parallel at their distal ends and are more angled from each other at their proximal ends.

21. The assembly of claim 20, wherein the two outermost passageways are disposed at respective angles of about 13° from a vertical medial plane of the hub body at their proximal ends.

22. The assembly of claim 12, wherein the centermost passageway is angled upwardly at an angle of up to about 5° from horizontal.

23. An assembly of a triple lumen implantable catheter, three extension tubes and a hub, comprising:
   a catheter adapted for implantation into vasculature of a patient and including at least a proximal end portion and three lumens extending therethrough for fluid transmission;
   three extension tubes each associated with a selected one of the three lumens of the catheter;
   wherein the proximal end portion of the catheter is skived and defines first and second selected lengths of two of the lumens, wherein the first and second lengths differ in length from each other, and
   an insert-molded hub body integrally joining the proximal end portion of the catheter to distal end portions of the three extension tubes and providing passageways extending and establishing sealed fluid communication between each extension tube and a respective selected one of the three lumens of the catheter, and
   a centermost of the passageways extending proximally and upwardly at a selected small angle from horizontal, and outermost ones of the passageways extend proximally and laterally outwardly at selected respective small angles from a vertical medial plane through the hub body.

24. The assembly of claim 23, wherein the two outermost passageways are disposed at respective angles of about 13° from a vertical medial plane of the hub body at their proximal ends.

25. The assembly of claim 23, wherein the centermost passageway is angled upwardly at an angle of up to 5° from horizontal.

* * * * *